United States Patent [19]

Durant et al.

[11] 4,285,952
[45] Aug. 25, 1981

[54] PYRIDYL, THIAZOLYL AND ISOTHIAZOLYL ALKYL BISAMIDINES

[75] Inventors: Graham J. Durant, Welwyn Garden City; Peter D. Miles, Hitchin, both of England

[73] Assignee: Smith Kline & French Laboratories Limited, Welwyn Garden City, England

[21] Appl. No.: 93,366

[22] Filed: Nov. 13, 1979

Related U.S. Application Data

[62] Division of Ser. No. 902,145, May 2, 1978, Pat. No. 4,212,875.

[30] Foreign Application Priority Data

May 5, 1977 [GB] United Kingdom ............... 18881/77

[51] Int. Cl.$^3$ .................. A61K 31/44; A61K 31/425; C07D 213/54; C07D 213/60; C07D 277/30; C07D 277/32; C07D 275/05

[52] U.S. Cl. ..................... 424/263; 424/270; 546/291; 546/296; 546/300; 546/305; 546/306; 546/330; 546/332; 548/186; 548/189; 548/202; 548/203; 548/204; 548/205; 548/213; 548/214

[58] Field of Search ............... 546/291, 296, 300, 305, 546/306, 330, 332; 548/186, 189, 202, 203, 205, 204, 213, 214; 424/263, 270

[56] References Cited

U.S. PATENT DOCUMENTS

| 4,034,101 | 7/1977 | Durant et al. ................ 548/342 |
| 4,062,967 | 12/1977 | Durant et al. ................ 548/342 |

FOREIGN PATENT DOCUMENTS

1305549  2/1973  United Kingdom .

*Primary Examiner*—Henry R. Jiles
*Assistant Examiner*—Natalia Harkaway
*Attorney, Agent, or Firm*—Joan S. Keps; Richard D. Foggio; Alan D. Lourie

[57] ABSTRACT

Bisamidines carrying one unsaturated nitrogen heterocycle-containing substituent, representative of which is 1-[N'-(2-(5-methyl-4-imidazolyl)methylthio)ethyl)-guanidino]-8-[N'-methylguanidino]octane, are histamine $H_2$-antagonists.

11 Claims, No Drawings

PYRIDYL, THIAZOLYL AND ISOTHIAZOLYL ALKYL BISAMIDINES

This is a division of application Ser. No. 902,145 filed May 2, 1978 now U.S. Pat. No. 4,212,875.

This invention relates to bisamidine compounds, to their preparation, to pharmaceutical compositions containing them, and to methods of blocking histamine $H_2$-receptors by administering these compounds.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine, diphenhydramine and chlorpheniramine are typical examples, are mediated through histamine $H_1$-receptors (Ash and Schild, *Brit. J. Pharmac. Chemother.*, 27, 427, (1966)), and drugs with this activity are hereinafter referred to as histamine $H_1$-antagonists. However, others of the biological actions of histamine are not inhibited by histamine $H_1$-antagonists and actions of this type which are inhibited by a compound described by Black et al. (*Nature*, 236, 385, (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by "antihistamines". Histamine $H_2$-antagonists are therefore useful, for example, as inhibitors of gastric acid secretion, as anti-inflammatory agents and as agents which act on the cardiovascular system, for example, as inhibitors of the effects of histamine on blood pressure. In the treatment of certain conditions, for example, inflammation and in inhibiting the actions of histamine on blood pressure, a combination of histamine $H_1$- and $H_2$- antagonists is useful.

The bisamidine compounds of the present invention are histamine $H_2$-antagonists.

British Patent Specifications Nos. 1,338,169, 1,397,436, 1,398,426, 1,421,792, 1,496,787 and 1,497,260 and German Offenlegungsschrift No. 2634433 disclose various different classes of compound of Structure 1:

Structure 1 where Het is a nitrogen-containing 5- or 6- membered heterocyclic ring such as imidazole, pyridine, thiazole, isothiazole, oxazole, isoxazole, triazole or thiadiazole, optionally substituted by lower alkyl, hydroxy, lower alkoxy, halogen, trifluoromethyl or amino; m is 0, 1 or 2 and n is 2 or 3 such that the sum of m and n is 3 or 4; Z is sulphur or a methylene group; X is sulphur, $CHNO_2$ or NY wherein Y is hydrogen, hydroxy, lower alkyl, cyano or $CONH_2$; and R is hydrogen or lower alkyl, as being useful histamine $H_2$-antagonists. A specific compound of Structure 1 is cimetidine (N-cyano-N'-methyl-N''-[2-((5-methyl-4-imidazolyl)methylthio)-ethylamino]guanidine), which has become a standard drug used in the treatment of duodenal and gastric ulcers.

Related compounds of Structure 2:

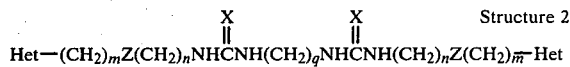

Structure 2 where q is from 2 to 8, and thus having two amidine groups —NH—C—NH— and two substituents each incorporating a heterocycle, are disclosed as histamine $H_2$-antagonists in British Patent Specification 1493931 and German Offenlegungschriften Nos. 2733951, 2733952 and 2733953.

It has now been discovered that a series of compounds in which the group R in Structure 1 is replaced by a

group, where q is an integer of from 2 to 12, have useful histamine $H_2$-antagonist activity. This involves a novel conception of compounds which have a markedly different chemical structure from those described above in that they contain two amidine groups to one heterocyclic substituent, and which exhibit the same type of activity as cimetidine although the two basic structural features of the molecule are not paired as in the publications referred to above. For example, one compound of this invention, 1-[N'-cyano-N''-(2-(5-methyl-4-imidazolylmethylthio)ethyl)guanidino]-2-[N''-cyano-N'-methylguanidino]ethane, is highly active when administered intravenously in the rat gastric acid secretion test.

The present invention provides compounds of Structure 3:

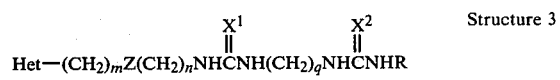

Structure 3 in which

Het is a 5- or 6- membered fully unsaturated heterocycle containing at least one nitrogen atoms, said heterocycle being imidazole, pyridine, thiazole, isothiazole, oxazole, isoxazole, triazole or thiadiazole, and optionally substituted by lower alkyl, trifluoromethyl, hydroxymethyl, halogen, hydroxy, lower alkoxy or amino:

Z is sulphur or methylene:

m is 0, 1 or 2, n is 2 or 3, and m+n is 3 or 4:

R is hydrogen or lower alkyl:

each of $X^1$ and $X^2$ is sulphur, a nitromethylene group $CHNO_2$, or an imino group NY, where Y is hydrogen, hydroxy, lower alkyl, cyano or carbamoyl $CONH_2$; and q is from 2 to 12.

Structure 3 is representative of the several tautomeric forms in which the compounds can exist.

The compounds are basic and can be prepared in the form of their acid addition salts, particularly their pharmaceutically-acceptable acid addition salts, as well as the free bases. Likewise where the compound has an imino group NH, it can be prepared in a protected form from which the free imino group can be readily regenerated by removal of the protecting group. An example of a protecting group is benzoyl, which is readily removed by acid hydrolysis; the imino group in protected form is the obvious chemical equivalent of the free imino group. A group NCN can be converted to NH by hydrolysis but in this specification is to be regarded as excluded from protected imino groups.

In this specification by 'lower alkyl' and 'lower alkoxy' are meant an alkyl or alkoxy group having from 1 to 4 carbon atoms: it can be straight or branched.

Preferably the group $(CH_2)_m$ is linked to a carbon atom of the heterocycle adjacent to a nitrogen atom. Preferably the heterocycle of Het is imidazole, particularly Het- is 2- or 4- imidazolyl optionally substituted by lower alkyl (especially methyl), halogen (especially chlorine or bromine), trifluoromethyl or hydroxymethyl. Especially valuable are compounds where Het- is a 5-methyl-4-imidazolyl group. Other suitable groups are 2-pyridyl optionally substituted by lower alkyl (especially methyl), lower alkoxy (especially methoxy), halogen, (especially chlorine or bromine), amino or hydroxy, 3-(1,2,4)-triazole, 2-thiazolyl, 3-isothiazolyl optionally substituted by chlorine or bromine, 3-(1,2,5)-thiadiazolyl optionally substituted by chlorine or bromine and 2-(5-amino-1,3,4-thiadiazolyl). Preferably m is 1, Z is sulphur and n is 2. $X^1$ and $X^2$ can be different, but preferably they are the same, particularly where $X^1$ and $X^2$ are both NY and Y is hydrogen or cyano, and where $X^1$ and $X^2$ are both $CHNO_2$. Preferably R is methyl: other examples of R are ethyl and n-propyl. Preferably q is 2 or 8.

Examples of specific compounds are:
1-[N'-(2-((5-methyl-4-imidazolyl)methylthio)ethyl)-guanidino]-2-[N'-cyano-N''-methylguanidino]ethane,
1-[N'-(2-((5-methyl-4-imidazolyl)methylthio)ethyl)-guanidino]-8-[N'-cyano-N''-methylguanidino]octane,
1-[N'-cyano-N''-(2-((5-methyl-4-imidazolyl)methylthio)ethyl)guanidino]-2-[N'-cyano-N''-methyl-guanidino]ethane,
1-[N'-cyano-N''-(2-((5-methyl-4-imidazolyl)methylthio)ethyl)guanidino]-8-[N'-cyano-N''-methyl-guanidino]octane, and
1-[N'-(2-(5-methyl-4-imidazolyl)methylthio)ethyl-guanidino]-8-[N'-methylguanidino]octane.

The bisamidines of Structure 3 where Z is sulphur can be prepared by a process in which the units of the structure represented by $Het—(CH_2)_m—$, $—Z(CH_2)_nNH—$, $—CX^1—$, $—NH(CH_2)_qNH—$, $—CX^2—$ and —NHR (designated units 1,2,3,4,5 and 6 respectively), are brought together in the correct sequence using as reagents compounds of the following structure for unit 1 $Het—(CH_2)_mCl$
for unit 2 $HS(CH_2)_nNH_2$
for unit 3 $(MeS)_2CX^1$
for unit 4 $NH_2(CH_2)_qNH_2$
for unit 5 $(MeS)_2CX^2$
for unit 6 $NH_2R$ with, if required, interconversion of one or both groups $X^1$ and $X^2$, to give the groups $X^1$ and $X^2$ required in the end-product.

Thus the unit 1 reagent can be reacted with the unit 2 reagent by known procedures to give the unit combination 12 of structure $Het(CH_2)_mS(CH_2)_nNH_2$; this can be reacted by known procedures with unit reagent 3 to give the unit combination 123 of structure $Het(CH_2)_mS(CH_2)_nNHCX^1SMe$; this can then be reacted by known procedures with unit reagent 4 to give the unit combination 1234 of structure $Het(CH_2)_mS(CH_2)_nNHCX^1NH(CH_2)_qNH_2$; operating by known procedures this can be reacted with unit reagent 5 to give the unit combination 12345 of structure $Het(CH_2)_mS(CH_2)_nNHCX^1NH(CH_2)_qNHCX^2SMe$; and finally this can be reacted by known procedures with the unit reagent 6 to give the unit combination 123456 which is the bisamidine of Structure 3.

The unit reagents have obvious chemical equivalents which can be employed in their stead. For instance Cl in unit reagent 1 can be replaced by bromine or arylsulphonyloxy (or other leaving groups disclosed in U.S. Pat. No. 4,013,678); and in unit reagents 3 and 5 the methylthio group can be replaced by lower alkylthio, arylthio, benzylthio, lower alkoxy, aryloxy or methylsulphinyl MeSO—.

The combination sequence can be in the reverse direction starting with the unit reagents 5 and 6 to give the unit combination 56 of structure $MeSCX^2NHR$, and adding the units 4, 3, 2 and 1 in that order. Furthermore, the building of the sequence can start with any other combination of units, for instance by reacting unit reagents 4 and 5 to give the 45 combination with $NH_2(CH_2)_qNHCX^2SMe$, and adding successively units 6, 3, 2 and 1. Where $X^1$ and $X^2$ are the same, the same unit reagent can be used to add units 3 and 5 simultaneously to a diamine providing unit 4. The Examples below illustrate a wide variety of combination sequences; for instance Examples 20, 31 and 32 taken together show the sequence 4+56, 3+456, 2+3456 and 1+23,456.

Preferably the combination sequence starts with a combination unit 12 of structure $Het—(CH_2)_mS(CH_2)_nNH_2$ (obtainable by well-known procedures) and the bisamidine is built from this. In preparing bisamidines of Structure 3 where Z is methylene, the combination unit 12 (obtainable by well-known procedures) is employed, and the sequence of process steps used is otherwise analogous to that used for bisamidines where Z is sulphur.

Care should be taken to use a sequence where one unit reagent or combination is not incompatible with another because of side-reactions with the group $X^1$ or $X^2$ present in another reagent. Thus a unit reagent or combination containing the reactive group —SMe is liable to react with the group $X^1$ or $X^2$ in a unit reagent or combination where this is a free imino group NH, and this is avoided by using a reagent with a protected imino group, such as benzoylimino NCOPh. Other reactive groups present, for instance an amino substituent of the heterocycle can be temporarily protected.

Where the groups $X^1$ and/or $X^2$ in the bisamidine are NY, where Y is hydroxy or lower alkyl, these are formed from the corresponding compounds where $X^1$ and/or $X^2$ are sulphur (neither $X^1$ nor $X^2$ being NH) by alkylation to the intermediate alkylthio compounds, for instance with methanolic hydrogen chloride or methyl iodide, and hydrolysis or reaction with hydroxylamine or the appropriate primary alkylamine. Where in the bisamidines $X^1$ and $X^2$ are $NCONH_2$, these are obtained by partial hydrolysis of the corresponding compounds where $X^1$ and $X^2$ are NCN. Bisamidines where $X^1$ and/or $X^2$ are NH can also be obtained by the hydrolysis of compounds where $X^1$ and/or $X^2$ are NCN or NCOPh.

In accordance with the above, the invention provides a process for preparing bisamidines of Structure 3, in which a compound of structure $Het—(CH_2)_mE$, where E is chlorine, $Z(CH_2)_nNH_2$, $Z(CH_2)_nNHCX^1SA, Z(CH_2)_nNHCX^1NH(CH_2)_qNH_2$, or $Z(CH_2)_nNHCX^1NH(CH_2)_qNHCX^2SA$ is reacted with the complementary compound of structure GNHR, where G is $HS(CH_2)_nNHCX^1NH(CH_2)_qNHCX^2—$, $ASCX^1NH(CH_2)_qNHCX^2—$, $NH_2(CH_2)_qNHCX^2—$, $ASCX^2—$ or hydrogen, where A is lower alkyl and each of $X^1$ and $X^2$ is S, $CHNO_2$, NH (including protected NH) or NCN, provided that where E is chlorine, Z is sulphur; and if required, where in the reaction product $X^1$ and/or $X^2$ are (a) S, these are converted by alkylation and reaction either with hydroxylamine to form a compound where $X^1$ and/or $X^2$ are NOH or with a primary lower alkylamine to form a compound where $X^1$ and/or $X^2$ are NY where Y is lower alkyl; (b) NCN, these are hydrolysed to form a compound where $X^1$ and/or $X^2$ are carbamoyl or NH; and (c) protected NH, these are subjected to a deprotection step to form a compound where $X^1$ and/or $X^2$ are free NH.

The complementary pairs of reagents are thus
$Het—(CH_2)_mCl$ and
$HS(CH_2)_nNHCX^1NH(CH_2)_qNHCX^2NHR$
$Het—(CH_2)_mZ(CH_2)_nNH_2$ and
$ASCX^1NH(CH_2)_qNHCX^2NHR$
$Het—(CH_2)_mZ(CH_2)_nNHCX^1SA$ and
$NH_2(CH_2)_qNHCX^2NHR$
$Het—(CH_2)_mZ(CH_2)_nNHCX^1NH(CH_2)_qNH_2$ and
$ASCX^2NHR$
$Het—(CH_2)_mZ(CH_2)_nNHCX^1NH(CH_2)_qNHCX^2SA$ and $NH_2R$ The steps in the above process with the pairs of reagents correspond to end-steps in the sequence of structure building described earlier as the combination of structural units 1 with 23,456, 12 with 3456, 123 with 456, 1234 with 56, and 12,345 with 6.

In each instance the reaction involved is formation of a bond between carbon and a hetero atom by elimination of the groups at the site of junction: with the first pair the reaction eliminates HCl (in practice as NaCl) to effect formation of a C-S bond, and with the others the reaction eliminates the compound ASH to effect formation of a C-N bond.

The use of obvious chemical equivalents of the chlorine (such as bromine and arylsulphonyloxy) and the group SA (such as arylthio, aralkylthio, lower alkoxy, aryloxy and alkylsulphinyl) in the above process is to be considered as within the scope of the claims of the present invention.

Preferably A is a methyl group.

Compounds of Structure 3 where $X^1$ and/or $X^2$ are NCN can also be prepared from the corresponding compounds where $X^1$ and/or $X^2$ are sulphur, (neither $X^1$ nor $X^2$ being NH), by alkylation and subsequent reaction of the alkylthio compound obtained with cyanamide and a strong base such as sodium methoxide or potassium t-butoxide; or by reaction with a salt of cyanamide with a heavy metal such as lead, cadmium or mercury in a solvent such as acetonitrile or dimethylformamide.

In converting a compound of Structure 3 where $X^1$ and/or $X^2$ are NCN to a corresponding compound where they are $NCONH_2$ and NH respectively, acid hydrolysis can be used under mild conditions to effect partial hydrolysis or more severe ones to effect full hydrolysis.

In converting a compound of Structure 3 where $X^1$ and/or $X^2$ are protected NH groups to a corresponding compound where they are free imino groups, conditions suitable for removing the protecting group are employed: for instance acid hydrolysis can be used to remove a benzoyl group.

The compounds of Structure 3 that are pharmacologically active are those other than the compounds in which $X^1$ and $X^2$ are protected imino groups: these latter are useful as intermediates for conversion to the active compounds. The active compounds block histamine $H_2$-receptors; that is, they inhibit the biological actions of histamine which are not inhibited by "antihistamines" such as mepyramine but are inhibited by burimamide. For example, they inhibit histamine-stimulated secretion of gastric acid from the lumen-perfused stomachs of rats anaesthetised with urethine, at doses of from 0.5 to 256 micromoles per kilogram intravenously. Their activity as histamine $H_2$-antagonists is also demonstrated by their ability to inhibit other actions of histamine which are not mediated by histamine $H_1$-receptors. For example, they inhibit the actions of histamine on the isolated guinea pig atrium and isolated rat uterus. They inhibit the basal secretion of gastric acid and also that stimulated by pentagastrin or by food. In a conventional test such as the measurement of blood pressure in the anaesthetised cat, at doses of from 0.5 to 256 micromoles per kilogram intravenously, they inhibit the vasodilator action of histamine. The potency of the compounds is illustrated by an effective dose producing 50% inhibition of gastric acid secretion in the anaesthetised rat and 50% inhibition of histamine-induced tachycardia in the isolated guinea pig atrium (less than $10^{-4}$ Molar).

For therapeutic use, the pharmacologically active compounds will normally be administered as a pharmaceutical composition comprising at least one such compound in the basic form or in the form of its addition salt with a pharmaceutically acceptable acid and in association with a pharmaceutical diluent or carrier. Such addition salts include those with hydrochloric, hydrobromic, hydriodic, sulphuric and maleic acids and may conveniently be formed from the corresponding bases by standard procedures, for example by treating the base with an acid in a lower alkanol or by the use of ion exchange resins to form the required salt either directly from the base or from a different addition salt.

Pharmaceutical compositions comprising a pharmaceutical carrier and a pharmacologically-active compound of the invention of Structure 3 in the basic form or in the form of its pharmaceutically-acceptable acid addition salts are also objects of this invention. The pharmaceutical carrier employed can be a solid or liquid. Examples of solid carriers are lactose, terra alba, sucrose, talc, gelatin, agar, pectin, acacia, magnesium stearate and stearic acid. Examples of liquid carriers are syrup, peanut oil, olive oil and water.

If a solid carrier is used, the composition can be prepared in the form of a tablet, capsule, troche or lozenge. The amount of solid carrier in a unit dosage form is generally from about 25 mg to about 300 mg. If a liquid carrier is used, the composition can be in the form of a syrup, emulsion, soft gelatin capsule, a sterile injectable liquid contained for example in an ampoule, or an aqueous or non-aqueous liquid suspension. The pharmaceutical compositions are prepared by conventional techniques involving procedures such as mixing, granulating and compressing or dissolving the ingredients as appropriate to the desired preparation.

The active ingredient is present in the compositions in an effective amount to block histamine $H_2$-receptors.

Preferably, each dosage unit contains the active ingredient in an amount of from about 50 mg to about 250 mg.

Methods of blocking histamine $H_2$-receptors which comprise administering to an animal a pharmacologically active compound of the invention of Structure 3 in the basic form or in the form of its pharmaceutically-acceptable acid addition salts, including the pharmaceutical compositions containing them, are also objects of the invention.

The active ingredient is preferably administered from one to six times per day. The daily dosage regimen will generally be from about 150 mg to about 1500 mg.

The route of administration may be oral or parenteral.

The invention is illustrated but not limited by the following Examples in which temperatures are in °C.

EXAMPLE 1

N-[2-((5-methyl-4-imidazolyl)methylthio)ethyl]-S-methylisothiourea hydriodide (3.72 g) and N-(2-aminoethyl)-N'-cyano-N''-methylguanidine (1.41 g) were dissolved in isopropyl alcohol (25 ml) and the mixture was heated under reflux for 6 hours. The solution was allowed to cool and the solid which crystallised out was filtered off and recrystallised from ethanol/isopropyl alcohol to give 1-[N'-(2-(5-methyl-4-imidazolyl)methylthio)ethyl)guanidino]-2-[N'-cyano-N''-methylguanidino]ethane as the hydriodide. (1.8 g), m.p. 164°–165°: Found: C, 33.85; H, 5.3; N, 26.8; S, 6.8; I, 27.15. $C_{13}H_{23}N_9S \cdot HI$ requires: C, 33.55; H, 5.2; N, 27.1; S, 6.9; I, 27.3%.

EXAMPLE 2

(a) Reaction of N-cyano-N'-[2-((5-methyl-4-imidazolyl)-methylthio)ethyl]-S-methylisothiourea with excess 1,2-diaminoethane at room temperature gave N-cyano-N'-(2-aminoethyl)-N''-[2-((5-methyl-4-imidazolyl)methylthio)ethyl]guanidine, m.p. 164°–167°.

(b) The product of (a) (8.4 g) and N-cyanodimethyldithioimidocarbonate (5.8 g) were dissolved in isopropyl alcohol (50 ml) and the mixture was heated under reflux for 1 hour, and allowed to cool. Solid was filtered off, washed with ether and recrystallised from methanol to give N-cyano-N'-[2-(N-cyano-S-methylisothioureido)ethyl]-N''-[2-((5-methyl-4-imidazolyl)methylthio)ethyl]-guanidine (8.1 g), m.p. 115°–116°. This latter compound (4.05 g) was dissolved in 50 ml of a 33% solution of methylamine in ethanol and the mixture was heated under reflux for 3 hours, and evaporated to an oil. Crystallisation from aqueous isopropyl alcohol and recrystallisation from water gave 1-[N'-cyano-N''-(2-(5-methyl-4-imidazolyl)methylthio)ethyl)guanidino]-2-[N'-cyano-N''-methylguanidino]ethane (1.0 g), m.p. 120°–124°: Found: C, 46.35; H, 6.1; N, 38.7; S, 8.8. $C_{14}H_{22}N_{10}S$ requires: C, 46.4; H, 6.1; N, 38.7; S, 8.9%.

EXAMPLES 3 to 13

A process is carried out as in Example 1, but using corresponding amounts of each of the following compounds instead of N-[2-((5-methyl-4-imidazolyl)methylthio)ethyl]-S-methylisothiourea:

N-[2-((4-imidazolyl)methylthio)ethyl]-S-methylisothiourea,
N-[2-((5-bromo-4-imidazolyl)methylthio)ethyl]-S-methylisothiourea,
N-[2-((3-chloro-2-pyridyl)methylthio)ethyl]-S-methylisothiourea,
N-[2-((3-methoxy-2-pyridyl)methylthio)ethyl]-S-methylisothiourea,
N-[2-((2-thiazolyl)methylthio)ethyl]-S-methylisothiourea,
N-[2-((3-isothiazolyl)methylthio)ethyl]-S-methylisothiourea,
N-[2-((2-oxazolyl)methylthio)ethyl]-S-methylisothiourea,
N-[2-((3-isoxazolyl)methylthio)ethyl]-S-methylisothiourea,
N-[2-((2-(1,3,4)-thiadiazolyl)methylthio)ethyl]-S-methylisothiourea,
N-[2-((3-(1,2,4)-triazolyl)methylthio)ethyl]-S-methylisothiourea and
N-[4-(4-imidazolyl)butyl]-S-methylisothiourea.

The products obtained are respectively:
Example No.
3. 1-[N'-(2-((4-imidazolyl)methylthio)ethyl)guanidino]-2-[N'-cyano-N''-methylguanidino]ethane
4. 1-[N'-(2-((5-bromo-4-imidazolyl)methylthio)ethyl)-guanidino]-2-[N'-cyano-N''-methylguanidino]ethane
5. 1-[N'-(2-((3-chloro-2-pyridyl)methylthio)ethyl)-guanidino]-2-[N'-cyano-N''-methylguanidino]ethane
6. 1-[N'-(2-((3-methoxy-2-pyridyl)methylthio)ethyl)-guanidino]-2-[N'-cyano-N''-methylguanidino]ethane
7. 1-[N'-(2-((2-thiazolyl)methylthio)ethyl)guanidino]-2-[N'cyano-N''-methylguanidino]ethane
8. 1-[N'-(2-((3-isothiazolyl)methylthio)ethyl)-guanidino]-2-[N'-cyano-N''-methylguanidino]ethane
9. 1-[N'-(2-((2-oxazolyl)methylthio)ethyl)guanidino]-2-[N'-cyano-N''-methylguanidino]ethane
10. 1-[N'-(2-((3-isoxazolyl)methylthio)ethyl)guanidino]-2-[N'-cyano-N''-methylguanidino]ethane
11. 1-[N'-(2-((2-(1,3,4)-thiadiazolyl)methylthio)ethyl)-guanidino]-2-[N'-cyano-N''-methylguanidino]ethane
12. 1-[N'-(2-((3-(1,2,4)-triazolyl)methylthio)ethyl)-guanidino]-2-[N'-cyano-N''-methylguanidino]ethane
13. 1-[N'-(4-(4-imidazolyl)butyl)guanidino]-2-[N'-cyano-N''-methylguanidino]ethane

EXAMPLES 14 to 19

Use of N-cyano-N'-[2-(85-methyl-4-imidazolyl)methylthio)ethyl]-S-methylisothiourea in the process of Example 2(a) with each of 1,3-diaminopropane, 1,4-diaminobutane, 1,7-diaminoheptane, 1,8-diaminooctane, 1,10-diaminodecane and 1,12-diaminododecane; yields respectively the following compounds:
N-cyano-N'-(3-aminopropyl)-N''-[2-((5-methyl-4-imidazolyl)-methylthio)ethyl]guanidine
N-cyano-N'-(4-aminobutyl)-N''-[2-((5-methyl-4-imidazolyl)-methylthio)ethyl]guanidine, m.p. 109°–111°
N-cyano-N'-(7-aminoheptyl)-N''-[2-((5-methyl-4-imidazolyl)-methylthio)ethyl]guanidine, m.p. 84°–87°
N-cyano-N'-(8-aminooctyl)-N''-[2-((5-methyl-4-imidazolyl)-methylthio)ethyl]guanidine, m.p. 122°–124°
N-cyano-N'-(10-aminodecyl)-N''-[2-((5-methyl-4-imidazolyl)-methylthio)ethyl]guanidine
N-cyano-N'-(12-aminododecyl)-N''-[2-((5-methyl-4-imidazolyl)-methylthio)ethyl]guanidine.

On reaction of these products first with N-cyanodimethyldithioimidocarbonate and then with methylamine according to the procedure of Example 2(b) the following products are obtained:
Example No.

14. 1-[N'-cyano-N''-(2-((5-methyl-4-imidazolyl)methylthio)-ethyl)guanidino]-3-[N'-cyano-N''-methylguanidino]propane
15. 1-[N'-cyano-N''-(2-((5-methyl-4-imidazolyl)methylthio)-ethyl)guanidino]-4-[N'-cyano-N''-methylguanidino]butane
16. 1-[N'-cyano-N''-(2-((5-methyl-4-imidazolyl)methylthio)-ethyl)guanidino]-7-[N'-cyano-N''-methylguanidino]heptane
17. 1-[N'-cyano-N''-(2-((5-methyl-4-imidazolyl)methylthio)ethyl)-guanidino]-8-[N'-cyano-N''-methylguanidino]octane, m.p. 79°–81°
18. 1-[N'-cyano-N''-(2-((5-methyl-4-imidazolyl)methylthio)-ethyl)guanidino]-10-[N'-cyano-N''-methylguanidino]decane
19. 1-[N'-cyano-N''-(2-((5-methyl-4-imidazolyl)methylthio)ethyl)-guanidino]-12-[N'-cyano-N''-methylguanidino]dodecane

EXAMPLE 20

(a) A mixture of 1,8-diaminooctane (14.1 g) with N-cyano-N'-methyl-S-methyl isothiourea (5.2 g) was maintained at 60° for 5 hours to give a solid product which was washed with ether and recrystallised from acetonitrile/ether to give N-cyano-N'-methyl-N''-(8-aminooctyl)guanidine (5.3 g) m.p. 81°–83°

(b) The product of (a) (2.22 g) and N-cyano-N'-[2-(85-methyl-4-imidazolyl)methylthio)ethyl]-S-methylisothiourea (2.4 g) were heated in pyridine (25 ml) under reflux for 12 hours. Evaporation of the reaction mixture yielded on oily residue which was chromatographed on a silica gel gel column with a 1:4 mixture of isopropyl alcohol and ethyl acetate. Evaporation of the eluent gave 1-[N'-cyano-N''-(2-((5-methyl-4-imidazolyl)methylthio)ethyl)guanidino]8-[N'-cyano-N'''-methylguanidino]octane (0.7 g) as a glass. This compound was shown to be identical with that prepared in Example 17.

EXAMPLE 21

The product of Example 1 was heated under reflux with an excess of 12 N hydrochloric acid for 6 hours and the mixture then evaporated to dryness. The residue was recrystallised from isopropyl alcohol to give 1-[N'-(2-((5-methyl-4-imidazolyl)methylthio)ethyl)-guanidino]-2-[N'-methylguanidino]ethane trihydrochloride, m.p. 194°–200°.

EXAMPLE 22

The product of Example 20 was heated under reflux with an excess of 12 N hydrochloric acid for 10 hours and evaporated to low volume. This solution was basified by the addition of a basic polyamine polystyrene ion-exchange resin cross-linked with 2% divinylbenzene (OH⁻ form) and the solution was evaporated to dryness to give 1-[N'-(2-((5-methyl-4-imidazolyl)methylthio)ethyl)guanidino]-8-[N'-methylguanidino]octane. To this product was added an excess of hydrochloric acid and the solution evaporated to dryness to give the trihydrochloride which was a glass; nmr:- (100 MHz. $D_2O$) 1.4 (m,$(CH_2)_6$), 2.32(s,$CH_3$), 2.76(m,$(CH_2S)$), 2.84(s,$(NHCH_3)$), 3.19(m($2xNCH_2$)), 3.42(m,$NCH_2$), 3.89(s,$CH_2S$), 8.59(s,Imid2-H).

EXAMPLE 23

A solution of S-methyl-N-[2-((5-methyl-4-imidazolyl)-methylthio)ethyl]dithiocarbamate (5 g) in ethanol (60 ml) is added to a solution of sodium (0.3 g) in ethanol (100 ml) and after filtration a solution of excess 1,8-diaminooctane (1.4 g) in ethanol (30 ml) is added and the mixture heated under reflux for 24 hours. Concentration of this reaction mixture yields N-(8-aminooctyl)-N'-[2-((5-methyl-4-imidazolyl)methylthio)ethyl]-thiourea, which when reacted first with N-cyanodimethyldithioimidocarbonate and then with methylamine according to the procedure of Example 2(b), yields 1-[N'-((2-(5-methyl-4-imidazolyl)methylthio)ethyl)thioureido]-8-[N'-cyano-N''-methylguanidino]octane.

EXAMPLE 24

Use in the process of Example 2(b) of 1,1-dimethylthio-2-nitroethylene instead of N-cyanodimethyldithioimidocarbonate gives 1-[2-(N'-cyano-N''-(2-((5-methyl-4-imidazolyl)methylthio)-ethyl)guanidino]ethylamino]-1-methylamino-2-nitroethylene.

EXAMPLE 25

Reaction of N-(8-aminooctyl)-N'-[2-((5-methyl-4-imidazolyl)-methylthio)ethyl]thiourea (see Example 22) with N,S-dimethyldithiocarbamate yields 1-[N'-(2-((5-methyl-4-imidazolyl)methylthio)ethyl)thioureido]-8-[N'-methylthioureido]octane.

EXAMPLE 26

Dry hydrogen chloride is bubbled through a solution of the product of Example 25 in methanol at 80° and the solvent removed, to give 1-[N'-(2-((5-methyl-4-imidazolyl)methylthio)-ethyl)-S-methylisothioureido]-8-[N',S-dimethylisothioureido]-octane. Reaction of this with at least two equivalents of hydroxylamine hydrochloride yields 1-[N'-hydroxy-N''-(2-((5-methyl-4-imidazolyl)methylthio)ethyl)guanidino]-2-[N'-hydroxy-N''-methylguanidino]ethane.

EXAMPLE 27

Reaction of the bis-S-methyl intermediate of Example 26 with methylamine according to the procedure of Example 2(b) yields 1-[N'-methyl-N''-(2-((5-methyl-4-imidazolyl)methylthio)ethyl)guanidino]-8-[N',N''-dimethylguanidino]octane.

EXAMPLE 28

Hydrolysis of the product of Example 2 with dilute hydrochloric acid at 40° yields 1-[N'-carbamoyl-N''-(2-((5-methyl-4-imidazolyl)methylthio)ethyl)guanidino]-2-[N'-carbamoyl-N''-methylguanidino)]ethane.

EXAMPLE 29 and 30

Use in the process of Example 2 of ammonia and ethylamine instead of methylamine gives respectively:
1-[N'-cyano-N''-(2-((5-methyl-4-imidazolyl)methylthio)ethyl)guanidino]-2-[N'-cyanoguanidino]ethane (Example 29)
1-[N'-cyano-N''-(2-((5-methyl-4-imidazolyl)methylthio)ethyl)guanidino]-2-[N'-cyano-N''-ethylguanidino]ethane (Example 30).

EXAMPLE 31

(a) N-Cyano-N'-methyl-N''-(8-aminooctyl)guanidine (see Example 20) is heated under reflux with an equivalent amount of N-cyanodimethyldithioimidocarbonate in isopropyl alcohol for 1 hour to give N-cyano-N'-[8-(N-cyano-S-methylisothioureido)-octyl]-N''-methylguanidine.

(b) The latter product is mixed with excess 4-(2-aminoethylthiomethyl)-5-methylimidazole and heated to 130° for 6 hours to give the product of Example 20, which is isolated as there described.

EXAMPLE 32

(a) To the isolated intermediate of Example 31(a) suspended in ethanol is added an equivalent amount of cysteamine hydrochloride in water: an equivalent amount of aqueous sodium hydroxide is added to liberate the cysteamine and the mixture heated under reflux for 1 hour. Ethanol is removed by evaporation and water added to precipitate 1-[N'-cyano-N"-(2-mercaptoethyl)guanidino]-8-[N'-cyano-N"-methylguanidino]octane.

(b) A solution of the dried product of (a) (1 mol) in dry ethanol is added to sodium ethoxide (2 mols) in ethanol under nitrogen with stirring, and stirring continued for 1 hour at ambient temperature. Powdered 5-methyl-4-chloromethylimidazole hydrochloride (1 mol) was added gradually to the solution which was stirred at ambient temperature for 1 hour and then heated at reflux temperature for 30 minutes, cooled, filtered and the product of Example 20 isolated as there described.

EXAMPLE 33

(a) 1,8-Diaminooctane (14.1 g) and N-cyanodimethyldithioimidocarbonate (29.2 g) in isopropyl alcohol (100 ml) were heated under reflux for 2 hours: the reaction mixture was cooled and the product crystallised from solution, and recrystallised from dimethylformamide/ether to give bis-1,8-(N-cyano-S-methylisothioureido)octane (25 g), m.p. 195°–197°.

(b) The product of (a) (17 g) and 4-(2-aminoethylthiomethyl)-5-methylimidazole (6.8 g) were dissolved in a mixture of pyridine (75 ml) and isopropyl alcohol (20 ml), and the mixture heated under reflux for 16 hours. The product, 1-[N'-cyano-N"-(2-(5-methyl-4-imidazolyl)methylthio)ethyl)guanidino]-8-[N'-cyano-S-methylthioureido]octane (2.2 g) m.p. 92°–100° crystallised out on cooling.

(c) The product of (b) in ethanol is heated under reflux with methylamine for 2 hours, and then evaporated to dryness to give 1-[N'-cyano-N"-(2-(5-methyl-4-imidazolyl)methylthio)ethylguanidino]-8-[N'-cyano-N"-methylguanidino]octane.

EXAMPLE 34

(a) A mixture of N-benzoyl-N'-methyl-S-methylisothiourea and an excess of 1,8-diaminooctane is maintained at 60° for 5 hours to give a solid product which is washed with ether to leave N-benzoyl-N'-methyl-N"-(8-aminooctyl)guanidine.

(b) This benzoylguanidine is used instead of the N-(2-aminoethyl)-N'-cyano-N"-methylguanidine in the process of Example 1, employing an equivalent amount, and there is obtained 1-[N'-(2-((5-methyl-4-imidazolyl)-methylthio)ethyl)guanidino]-8-[N'-benzoyl-N"-methylguanidino]octane.

EXAMPLE 35

The product of Example 24 is heated in 1ON hydrochloric acid at 100° for 6 hours, cooled, filtered to remove benzoic acid: the solution is evaporated to dryness to give 1-[N'-(2-((5-methyl-4-imidazolyl)methylthio)ethyl)guanidino]-8-[N'-methylguanidino]octane trihydrochloride.

EXAMPLE 36

The process of Example 33(a) is carried out using the equivalent amount of N-benzoyl-dimethyldithioimidocarbonate instead of N-cyanodimethyldithioimidocarbonate, to give bis-1,8-(N-benzoyl-S-methylisothioureido)octane: this is used in the process of Example 33 (b) to give 1-[N'-benzoyl-N"-(2-(5-methyl-4-imidazolyl)methylthio)ethyl)guanidino]-8-[N'-benzoyl-S-methylthioureido]octane, which is reacted with methylamine to give 1-[N'-benzoyl-N"-(2-(5-methyl-4-imidazolyl)-methylthio)ethylguanidino]-8-[N'-benzoyl-N"-methylguanidino]-octane.

EXAMPLE 37

Hydrolysis or the product of Example 36 with hydrochloric acid using the procedure of Example 22 gives the product of Example 22.

EXAMPLE 38

A pharmaceutical composition is prepared from the following ingredients:
1-[N'-cyano-N"'-(2-((5-methyl-4-imidazolyl)-methylthio)ethyl)guanidino]-2-[N'-cyano-N"-methylguanidino]ethane: 150 mg
Sucrose: 75 mg.
Starch: 25 mg
Talc: 5 mg
Stearic acid: 2 mg
The ingredients are screened, mixed and filled into a hard gelatin capsule.

EXAMPLE 39

An injectable pharmaceutical composition is prepared by dissolving 1-[N'-(2-(5-methyl-4-imidazolyl)-methylthio)-ethylguanidino]-8-[N'-methylguanidino]octane trihydrochloride (100 g) in sterile water (2 liters). From it are prepared ampoules containing 100 mg of active ingredients.

Similarly, other compounds of Structure 3 can be formulated as pharmaceutical compositions by the procedures of Examples 38 and 39.

The pharmaceutical compositions prepared in the foregoing Examples are administered to a subject within the dose range given above to block histamine $H_2$-receptors.

What is claimed is:

1. A compound of the structure

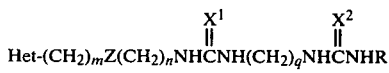

in which

Het is a 5- or 6-membered fully unsaturated heterocycle containing at least one nitrogen atom, said heterocycle being pyridine optionally substituted by lower alkyl, trifluoromethyl, hydroxymethyl, halogen, hydroxy, lower alkoxy or amino; or thiazole or isothiazole which are attached at a ring carbon and which are optionally substituted by lower alkyl, trifluoromethyl, hydroxymethyl, halogen or lower alkoxy;

Z is sulphur or methylene;

m is 0, 1 or 2, n is 2 or 3, and m+n is 3 or 4;

R is hydrogen or lower alkyl;

each of $X^1$ and $X^2$ is sulphur, a nitromethylene group $CHNO_2$, or an imino group NY, where Y is hydrogen, hydroxy, lower alkyl, cyano or carbamoyl $CONH_2$; and q is from 2 to 12;

in the form of the free base or its pharmaceutically-acceptable acid addition salts.

2. A compound according to claim 1, in which the group $(CH_2)_m$ is linked to a carbon atom of the heterocycle adjacent to a nitrogen atom.

3. A compound according to claim 1, in whixh Z is sulphur, m is 1 and n is 2.

4. A compound according to claim 1, in which q is 2.

5. A compound according to claim 1, in which q is 8.

6. A compound according to claim 1, in which R is methyl.

7. A compound according to claim 1, in which both $X^1$ and $X^2$ are NY.

8. A compound according to claim 1, in which both $X^1$ and $X^2$ are NH.

9. A compound according to claim 7, in which both $X^1$ and $X^2$ are NCN.

10. A pharmaceutical composition to block histamine $H_2$-receptors comprising in an effective amount to block said receptors a compound of claim 1 in combination with a pharmaceutically-acceptable diluent or carrier.

11. A method of blocking histamine $H_2$-receptors which comprises administering to an animal in need thereof in an effective amount to block said receptors a compound of claim 1.

* * * * *